(12) United States Patent
Gaida et al.

(10) Patent No.: US 11,091,849 B2
(45) Date of Patent: Aug. 17, 2021

(54) BATH AND METHOD FOR FILLING A VERTICAL INTERCONNECT ACCESS OR TRENCH OF A WORK PIECE WITH NICKEL OR A NICKEL ALLOY

(71) Applicant: Atotech Deutschland GmbH, Berlin (DE)

(72) Inventors: Josef Gaida, Berlin (DE); Jan Sperling, Berlin (DE); Mauro Castellani, Berlin (DE); Grigory Vazhenin, Berlin (DE); Stefanie Ackermann, Berlin (DE); Heiko Brunner, Berlin (DE); Dirk Rohde, Berlin (DE)

(73) Assignee: Atotech Deutschland GmbH, Berlin (DE)

( * ) Notice: Subject to any disclaimer, the term of this patent is extended or adjusted under 35 U.S.C. 154(b) by 0 days.

(21) Appl. No.: 16/635,568

(22) PCT Filed: Sep. 13, 2018

(86) PCT No.: PCT/EP2018/074730
§ 371 (c)(1),
(2) Date: Jan. 31, 2020

(87) PCT Pub. No.: WO2019/053120
PCT Pub. Date: Mar. 21, 2019

(65) Prior Publication Data
US 2020/0199766 A1  Jun. 25, 2020

(30) Foreign Application Priority Data
Sep. 13, 2017 (EP) .................................. 17190805

(51) Int. Cl.
*C25D 3/18* (2006.01)
*C07D 401/10* (2006.01)
*C25D 3/56* (2006.01)
*C25D 7/12* (2006.01)
*H05K 3/42* (2006.01)

(52) U.S. Cl.
CPC ............ *C25D 3/18* (2013.01); *C07D 401/10* (2013.01); *C25D 3/562* (2013.01); *C25D 7/123* (2013.01); *H05K 3/421* (2013.01); *H05K 3/423* (2013.01); *H05K 2203/0723* (2013.01); *H05K 2203/0786* (2013.01)

(58) Field of Classification Search
None
See application file for complete search history.

(56) References Cited

U.S. PATENT DOCUMENTS

| | | | |
|---|---|---|---|
| 3,592,943 A * | 7/1971 | Passal | C25D 3/18 205/277 |
| 5,061,351 A | 10/1991 | Commander et al. | |
| 2008/0169006 A1 | 7/2008 | Musale et al. | |
| 2009/0188805 A1 | 7/2009 | Moffat et al. | |
| 2011/0168566 A1 * | 7/2011 | Berger | C25D 3/52 205/265 |
| 2012/0010434 A1 | 1/2012 | Tsutsuminai et al. | |

FOREIGN PATENT DOCUMENTS

EP    1489201 A2    12/2004
JP    2016008322 A *   1/2016

OTHER PUBLICATIONS

Machine translation of Najakima et al. JP 2016008322 A (Year: 2016).*
PCT/EP2018/074730; PCT International Search Report and Written Opinion of the International Searching Authority dated Oct. 5, 2018.

* cited by examiner

*Primary Examiner* — Wojciech Haske
(74) *Attorney, Agent, or Firm* — Renner, Otto, Boisselle & Sklar, LLP (57) ABSTRACT

An aqueous bath for filling a vertical interconnect access or trench of a work piece with nickel or a nickel alloy, the bath comprising
  a source of nickel ions, and optionally a source of ions of at least one alloying metal,
  at least one buffering agent,
  at least one of a dimer of a compound of formula (I) or mixtures thereof formula (I)

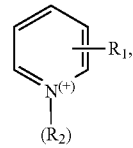

wherein
  $R_1$ is a substituted or unsubstituted alkenyl group,
  $R_2$ may be present or not, and if present $R_2$ is a $-(CH_2)_n-SO_3^-$ group, wherein n is an integer in the range of 1-6, and wherein one or more of the hydrogens in the group may be replaced by a substituent, preferably hydroxide; and
a method for filling a vertical interconnect access or trench of a work piece with nickel or a nickel alloy with said aqueous bath.

9 Claims, 8 Drawing Sheets

BATH AND METHOD FOR FILLING A VERTICAL INTERCONNECT ACCESS OR TRENCH OF A WORK PIECE WITH NICKEL OR A NICKEL ALLOY

The present application is a U.S. National Stage Application based on and claiming benefit and priority under 35 U.S.C. § 371 of International Application No. PCT/EP2018/074730, filed 13 Sep. 2018, which in turn claims benefit of and priority to European Application No. 17190805.6 filed 13 Sep. 2017, the entirety of both of which is hereby incorporated herein by reference.

FIELD OF THE INVENTION

The present invention relates to an aqueous bath for electrolytic deposition of nickel or a nickel alloy, a method for filling a vertical interconnect access or trench of a work piece with nickel or a nickel alloy, to the use of an aqueous bath for filling vertical interconnect accesses or trenches of a work piece with nickel or a nickel alloy in an electrodepositing process, and to compounds useful for said bath, method and use.

BACKGROUND OF THE INVENTION

Uniform metal deposition in structures such as trenches, blind micro vias (BMVs) or through hole vias (via=Vertical Interconnect Access) with nickel is often difficult: Because of the geometric arrangement and development of these structures they exhibit a variable electric depositing behavior. In particular, in very small structures of this type, influences of the diffusion of the metal ions and of the additives towards the deposition location are dominant. A uniform filling with nickel is the prerequisite for the development of complex conductor structures. An insufficient or non-uniform filling, often leads to their uselessness and consequently to the rejection of the entire printed circuit board or chip carrier. Void-free filling of vias is required for electrical interconnects for reliability reasons. Additionally, a subconformal or conformal deposition in these structures often leads to voids. A subconformal filling means that metal is deposited at the bottom and at the side wall of a via, wherein thickness of deposition at the wall increases from the bottom to the top of the via, so that during filling the via is closed at the top without complete filling and void-formation. A conformal deposition means that equal thickness of a deposition is reached on all surfaces, bottom and side wall of a via. This often leads to a void extending in the center of the via extending through the via until the top.

US20090188805A1 describes a process for electrodepositing at least one ferromagnetic material into a three dimensional pattern within a substrate. The process comprises providing a substrate material, dielectric or conductor, having a three dimensional recessed pattern in at least one outer surface thereof, dielectric substrate materials also having an electrical conductive seed layer at least within the three dimensional pattern. An electrolytic bath is prepared comprising at least one ferromagnetic material and at least one accelerating, inhibiting, or depolarizing additive. The at least one ferromagnetic material comprises at least one metal cation selected from the group consisting of $Ni^{2+}$, $Co^{2+}$, $Fe^{2+}$, $Fe^{3+}$, and combinations thereof. The substrate is placed into the electrolytic bath and the electrolytic bath contacts the conducting three dimensional patterns in the substrate or the conducting seed layer within the pattern on a dielectric substrate. A counter electrode is placed into the electrolytic bath. An electric current is passed through the electrolytic bath between the electrical conductive substrate or seed layer on the three dimensional substrate and the counter electrode. At least a portion of the ferromagnetic material is deposited into at least a portion of the three dimensional pattern wherein the at least one deposited ferromagnetic material is substantially void-free.

OBJECTIVE OF THE INVENTION

It is the objective of the present invention to provide a method for filling a vertical interconnect access or trenches of a work piece with nickel or a nickel alloy, wherein the filling should be void free or substantially void free, particularly in a vertical interconnect access.

SUMMARY OF THE INVENTION

This objective is solved by an aqueous bath, which is particularly suitable for filling a vertical interconnect access (also abbreviated as via), such as a blind via, preferably a blind micro via, or through hole via, or trenches of a work piece with nickel or a nickel alloy, the bath comprising
- a source of nickel ions, and optionally a source of ions of at least one alloying metal,
- at least one buffering agent,
- at least one of a dimer of a compound of formula (I) or mixtures thereof formula (I)

wherein
R$_1$ is a substituted or unsubstituted alkenyl group,
R$_2$ may be present or not, so that the nitrogen may be positively charged or not, and R$_2$, if present, is a —(CH$_2$)$_n$—SO$_3^-$ group, wherein n is an integer in the range of 1-6, an wherein one or more of the hydrogens in the —(CH$_2$)$_n$—SO$_3^-$ group may be replaced by a substituent, preferably hydroxide.
R$_1$ can be present in 2-position, 3-position or 4 position of the ring, preferably in 2-position or 3-position, more preferably in 2-position.
A preferable R$_1$ is vinyl.
If the —(CH$_2$)$_n$—SO$_3^-$ group carries one of more of a substituent at the carbon-chain, preferably hydroxide, one or two hydrogens in a —CH$_2$— moiety is/are replaced by said substituent.

The objective of the invention is also solved by a method for depositing nickel or nickel alloy on a work piece, particularly for filling a vertical interconnect access or trench of a work piece with nickel or a nickel alloy, the method comprising
a) contacting a work piece, the work piece preferably having at least one vertical interconnect access and/or at least one trench, and at least one anode with said aqueous bath, or with an aqueous bath as further described in specific embodiments,
b) providing an electric current flow between the work piece and the at least one anode, so that nickel or a nickel alloy is deposited on the work piece, preferably in the vertical interconnect access or trench.

The objective of the invention is also solved by the use of an aqueous bath as defined above for filling vertical interconnect accesses, preferably blind micro vias, or trenches of a work piece with nickel or a nickel alloy in an electrodepositing process.

The invention is in particular suitable for processing the work pieces in the manufacturing of electronic devices as printed circuit boards (PCBs) e.g. with high numbers of die-to-die connections using e.g. bridges or interposer.

The used work piece comprises in one embodiment recesses or recess structures e.g. having at least one vertical interconnect access and/or at least one trench. The recesses or recess structure are forming the basis of conductive metal circuits e.g. conductive metal lines or through connections if filled with nickel according to the present invention. The vias, preferably through silicon vias (TSV), have preferably aspect ratios (width or diameter:depth) of at least 1:3, more preferred 1:6 and most preferred more than 1:10. In some embodiments the vias have µm dimensions of e.g. 10×30 µm, 10×60 µm or 10×100 µm; the trenches have µm dimensions of e.g. width 20-2 µm and depth 20-2 µm, with ratios from 20×20 µm to 2×2 µm. The invention is preferably suited to fill these vias and/or trenches with void-free nickel.

In another embodiment the invention is suitable to build-up nickel pillars by filling vias which are formed during pattern or panel plating processes.

The recesses or recess structures comprise one or more first conductive metal layers as a seed layer or a sputtered metal layer which are provided by methods known to the skilled person.

The work pieces can also comprise already built conductive layers or conductive structures as fine circuit lines as copper or nickel layers or structures. These conductive layers or conductive structures can be connected with the recesses or recess structures by filling with nickel according to the invention.

The invention is also directed to a compound of formula (II)

formula (II)

wherein $R_2$ is a —$(CH_2)_n$—$SO_3^-$ group, wherein n is an integer in the range of 1-6 preferably 2-4, and wherein one or more of the hydrogens in the —$(CH_2)_n$—$SO_3^-$ group may be replaced by a substituent.

It has been shown that with a method of the invention or an aqueous bath of the invention a void free or substantially void free deposition of nickel or nickel alloy in a via or trench can be reached, even in vias (vertical interconnect access) that have a high aspect ratio (width or diameter: depth) of preferably up to 1:10.

The method and bath of the invention are particularly suitable for electrolytic deposition of nickel or nickel alloy on work pieces that are selected from wafers and printed circuit boards.

It has been surprisingly found that a dimer a compound of formula (I) or mixtures thereof can be used as via or trench filling additive and/or leveler in a nickel-electrodeposition process, i.e. in electrolytic deposition of nickel.

In the method of the invention or with an aqueous bath of the invention a bottom-up or a super-conformal filling of blind vias (via=vertical interconnect access) can be reached, leading to no or a minimum of voids. A bottom up filling means that a blind via is filled from the bottom to the top. A super-conformal filling means that metal is deposited at the bottom an at the side wall of a via, wherein thickness of deposition at the wall decreases from the bottom to the top of the via, so that a V-shaped intermediate structure is formed during filling. Moreover, in the method of the invention or with an aqueous bath of the invention very fast deposition of nickel or nickel alloy can be reached.

DETAILED DESCRIPTION OF THE INVENTION

Details of the invention and specific embodiments are described in this section.

Nickel alloy generally includes alloys that comprise nickel and thus includes also alloys wherein less than 50 weight-% are nickel. A nickel alloy may comprise 20 weight-% nickel. A nickel alloy may in another embodiment comprise 50 weight-% nickel. Beneficial nickel alloys are e.g. Permalloy with high magnetic permeability (80% Ni, 20% Fe), Invar with low thermal expansion (64% Fe, 36% Ni), Kovar with thermal expansion matched to glass (54% Fe, 29% Ni, 17% Co). Soft magnetic alloys like Permalloy can contain as low as 36% Ni. If the term nickel is used in this description, nickel alloys are also encompassed, if not stated otherwise.

For the purpose of the present invention the term "alkenyl" means a monovalent linear or branched unsaturated hydrocarbon moiety, having in the skeleton thereof but carbon atoms, wherein an alkenyl moiety comprises all conceivable isomers thereof. A specific alkenyl group is an omega alkenyl group, i.e. an alkenyl group having a double bond between the next-to-last carbon atom and the last carbon in the group, counted from the pyridine ring (i.e. the first carbon atom is the one connected to the pyridine ring).

The term "leveler" means the following: Using the aqueous, acid bath according to the invention and the method according to the invention, it is possible to deposit nickel in a very uniform manner in the structures that are to be filled, as recessions and depressions, particularly trenches and vias. In particular it is possible to fill recessions and depressions totally, reduce a deposition of nickel on the surface compared to deposition in the depressions/recessions, and to avoid or at least minimize any voids or dimples. This guarantees that an extensively smooth, even nickel surface is formed that exhibits practically no deformations. For example, dimples are hardly ever to be seen in the area of blind micro vias (abbreviated as BMVs), such that an ideal or almost ideal rectangular shape is produced in the cross-section of the conductor structure.

The source of nickel ions may be a nickel salt, such as nickel sulfamate, -sulfate, -chloride, -fluoroborate or a combination thereof.

The source of ions of at least one alloying metal is preferably a salt of such metal. In one embodiment, the alloying metal is selected from cobalt or iron or a combination thereof.

Abbreviations or variables in formulas (such as $R_1$ and $R_2$) have or may have the same meaning in this invention (if not otherwise indicated), regardless of whether an aqueous bath, a method, a use or a compound itself is described. So, specific meanings or preferred embodiments of abbreviations or variables may be applied throughout the whole invention, even if not repeated in a specific context.

The brackets which enclose $R_2$ and the positive charge in formula (I) mean that $R_2$ and the positive charge may be present or not. If $R_2$ is not present, the positive charge is not present as well.

In one embodiment of the invention, $R_1$ in formula (I) is a —$(CH_2)_m$—CH=$CH_2$ group, wherein m is an integer in the range of 0-4, preferably 0-2 (if m=0, $R_1$ is a vinyl group), and $R_2$, if present, is a —$(CH_2)_n$—$SO_3^-$ group, wherein n is an integer in the range of 1-4, preferably 1-3.

Dimers:

Hereinafter, specific dimers of a compound of formula (I) are described.

In one embodiment, said dimer of a compound of formula (I) is a compound of formula (II), formula (II)

In one embodiment, said dimer of a compound of formula (I) is a compound of formula (VII)

formula (VII)

Above dimers of formulas (II) and (VII) can be obtained by using a compound of formula (I) wherein $R_1$ is vinyl in 2-position. Dimers of formulas (II) and (VII) can be formed according to a reaction which is further described below with respect to dimers with specific meaning of $R_2$.

In a more specific embodiment, the compound of formula (I) is the compound of formula (III), which is also called 1-(3-Sulfopropyl)-2-vinylpyridinium:

formula (III)

A compound of formula (III) is available e.g. as 1-(3-Sulfopropyl)-2-vinylpyridinium betaine under CAS 6613-64-5.

In the invention, the compound of formula (III) is in state of a dimer or is transferable into a dimer.

In one embodiment, the dimer of the compound of formula (III) is a compound of formula (IV):

formula (IV)

Without wishing to be bound by theory, a compound of formula (IV) may be formed according to a Homo-Diels-Alder reaction starting with two compounds of formula (I), preferably of two compounds of formula (III), but the invention shall not be limited thereon:

formula (III)    formula (III)

formula (IV)

In another embodiment, the dimer of the compound of formula (III) is a compound of formula (VIII):

formula (VIII)

Without wishing to be bound by theory, a compound of formula (VIII) may be also be formed according to a Homo-Diels-Alder reaction starting with two compounds of formula (I), preferably of two compounds of formula (III), but the invention shall not be limited thereon. In comparison to above reaction mechanism, relative orientation of two compounds of formula (III) is different in the cycloaddition:

formula (III)

formula (III)

An analogue mechanism can be assumed for formation of a compound of formula (VII). Dimerization is assumed to be irreversible due to the last rearrangement step. A racemic mixture is assumed to be formed.

In one embodiment, the total concentration of the at least one of a dimer or mixtures thereof in the bath is 1-10000 mg/L, preferably 10-10000 mg/L, or 50-10000 mg/L, or 80-10000 mg/L, more preferably 80-1500 mg/L, even more preferred 100-1500 mg/L, or 100-1000 mg/L. The bath may further comprise 0-20 weight-%, preferably 0-10 weight-%, more preferred 0-5 weight-%, even more preferred 0 weight-% of compound of formula (I) (which is not dimer) based on the total amount of the used dimer or mixtures thereof according to said concentration above.

Any mixture of one or more dimers may be employed.

In this connection, the term at least one relates to the chemical structure, not to the number of molecules. So, if for example two dimers are employed, this means dimers of different chemical structure.

The term "buffering agent" means a weak acid or base used to maintain the acidity (pH) of the aqueous bath near a chosen value after the addition of another acid or base. A buffering agent may form, in the aqueous bath, a composition of a weak acid and the allocated base. Non limiting examples of suitable buffering agents are, or based on, boric acid, phosphoric acid, citric acid, acetic acid buffers. The buffering agent is preferably a buffering agent that leads to an acidic pH of the bath. So, the bath is preferably an acidic bath.

Hereinafter, further optional ingredients that may be added to the bath are disclosed:

Chloride ions may be added, particularly if in the method soluble anodes are used. In addition to an above mentioned source of nickel ions, which may be any suitable nickel salt, nickel chloride, may be added if in the method soluble anodes are used. Then, nickel chloride is used for activation of soluble anodes. Nickel chloride may also contribute to the source of nickel ions, i.e. nickel from the nickel chloride may also be deposited on the work piece.

The bath may comprise a brightener, also called brightening agent. The term "brightener" refers to substances that exert a brightening effect during the nickel deposition process, which particularly means that a brightener leads to bright deposits, which may be due (without wishing to bound by theory) to affecting microstructure by sulfur incorporation. The term brightener may also refer to substances that exert a smoothing effect on the surface deposited surface. An example of a suitable brightener is saccharine. The compound of above formula (II) also has the function of a brightener. So, an additional brightener, different from a compound of formula (II), may also be called "a further brightener".

The brightener may also fulfill the function of a stress reducer, also called a stress reducing agent. The term "stress reducer" refers to substances that reduce stress between distinct layers of deposited nickel or between a nickel layer and a work piece surface. Particularly, saccharine may also fulfill the function of a stress reducer.

The bath may comprise a wetting agent. The term "wetting agent" refers to substances that reduce surface tension of the aqueous bath and lead to better wetting of a work piece surface with the bath. In result, gas bubbles on a surface of a work piece are avoided or minimized by better wetting when the work piece surface is contacted with the bath. Non limiting examples of suitable wetting agents are cationic (such as cetyltrimethylammonium bromide), anionic (such as aliphatic sulfonates) and nonionic (such as polyethyleneglycol) surfactants.

Hereinafter, useful amounts of ingredients in a bath are disclosed. It is to be understood that ingredients and ranges can be combined with each other in any combination.

a) Source of nickel ions, particularly nickel salt:
   1-160 g/L, preferably 50-120 g/L
b) Source of ions of at least one alloying metal, particularly a metal salt, preferably a Co— or Fe-Salt:
   up to 50 g/L, preferably 1-50 g/L
c) Buffering agent:
   1-40 g/L, preferably 10-40 g/L
d) Dimer of a compound of formula (I) and mixtures thereof:
   1-10000 mg/L, preferably 100-1000 mg/L
e) Brightener, stress reducer:
   tested 0-50 g/L, preferably 0-10 g/L
f) Chloride (for soluble anode activation):
   0-80 g/L, preferably 2-10 g/L
g) Wetting agent:
   0-20 g/L, preferably 0-1 g/L Hereinafter, process parameters than can be used in the process of the invention are disclosed in non-limiting manner:

The method of the invention can be carried out as galvanostatic, potentiostatic, step, pulsed, or reversed pulsed electrodeposition method. So, deposition can be carried out in various regimes such as galvanostatic, potentiostatic, step, pulsed, or reversed pulsed regimes. A preferred, but not limiting method is galvanostatic deposition with one or several current steps.

A) Temperature of the bath:
20-80° C., preferably 40-60° C.
B) pH: 1-6, preferably 3-5
C) Current density:
0.1-100 ASD (ampere per square decimeter), preferably 0.1-50 ASD, or more preferred 0.5-25 ASD. These ranges are non-limiting. Optimal current density for filling depends strongly on concentration of components in the bath, size and aspect ratio of a work piece.
D) Stirring speed (stirring is optional): 0-3000 rpm. Stirring speed depends on the layout of the method equipment and is to be set in order to reach effective diffusion layer thickness.

EXAMPLES

The invention will now be illustrated by reference to the following non-limiting examples.

Example 1

Synthesis of a Dimer of a Compound of Formula (IV)

60 g of a compound of formula (III) were added to 40 g of water and heated to reflux for 96 h. A light brown solution was formed. Removal of the solvent gave 60 g of the dimer.

Figure 1:
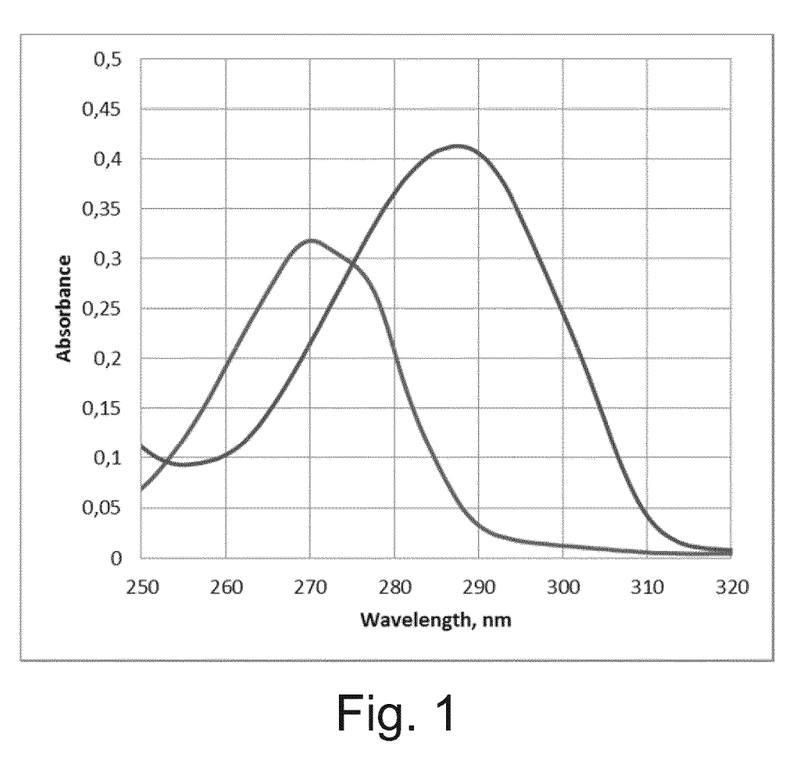
FIG. 1: UV-Vis spectra of monomer and dimer.

Characterization of the product was made by UV-Vis, IR-Spectroscopy, 1H-NMR, 13C-NMR, two-dimensional-NMR (2D-NMR) and liquid chromatography (LC)/HPLC. The results are as follows:

UV-Vis (LC-UV):
Results are shown in FIG. 1 at the end of the reaction. UV-Vis is sensitive to the size of the aromatic π system: saturation of vinyl group during dimerization leads to a blue shift of the absorption maximum from 289 nm to 270 nm. This was qualitatively confirmed by electronic structure calculations. However, formation of other species with smaller π system could also lead to a blue shift, so that further methods for characterization were applied.

Figure 2:
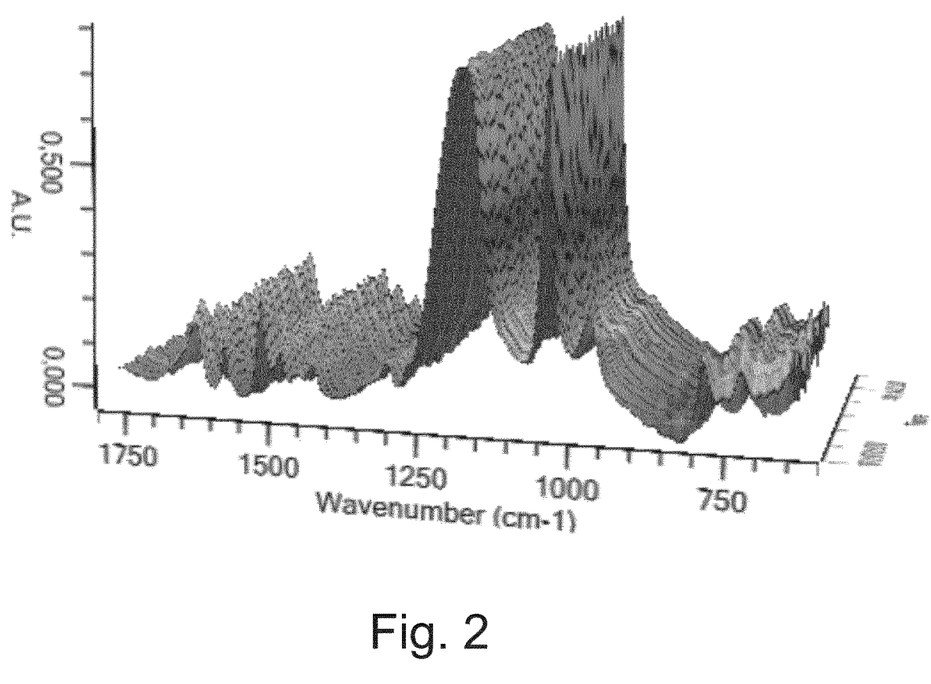
FIG. 2: IR spectrum of reaction mixture.

IR:
Results are shown in FIG. 2 at the end of the reaction. The method is sensitive to the vinyl group vibration mode around 950 $cm^{-1}$, which is shown in FIG. 2. This was confirmed by electronic structure calculations. This method can be used for monitoring reaction progress. This method quantifies consumption of monomer, not explicitly formation of dimer, so that further methods for characterization were applied.

Figure 3:
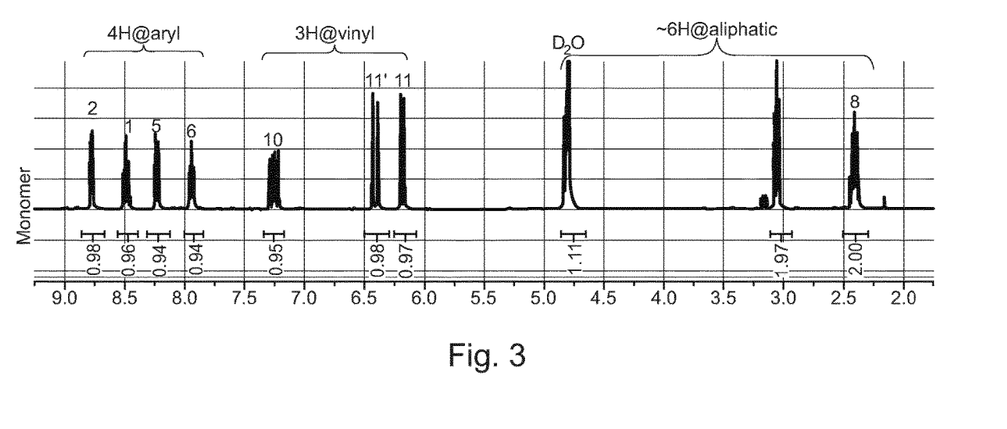
FIG. 3: 1H-NMR-spectrum of reaction mixture.

1H-NMR:
Results are shown in FIG. 3 at the end of the reaction. The results confirm a loss of the vinyl group. The results moreover confirm 4+2 cycloaddition as opposed to 2+2 cycloaddition based on the balance of aromatic to aliphatic protons. The method is not specific enough to distinguish two 4+2 isomers, so that further methods were applied.

Figure 4:
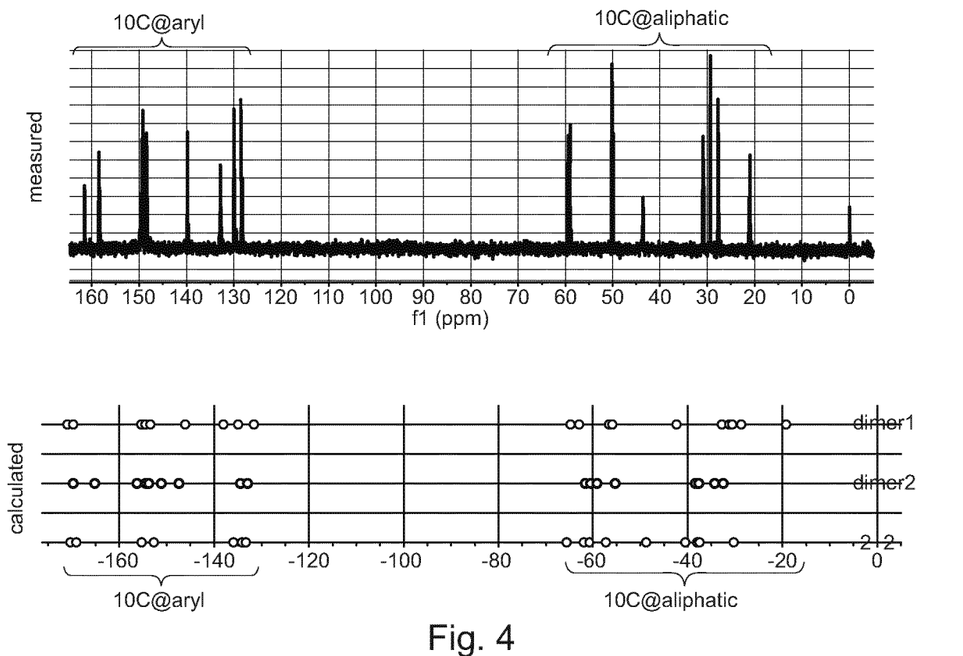
FIG. 4: 13C-NMR-spectrum of reaction mixture.

13C-NMR:
Results are shown in FIG. 4 at the end of the reaction. Modeling the spectrum allows for preliminary structure identification, showing that a compound of formula (IV) (called "dimer 1") is formed. "Dimer 2" is a compound of formula (VIII)

Figure 5:
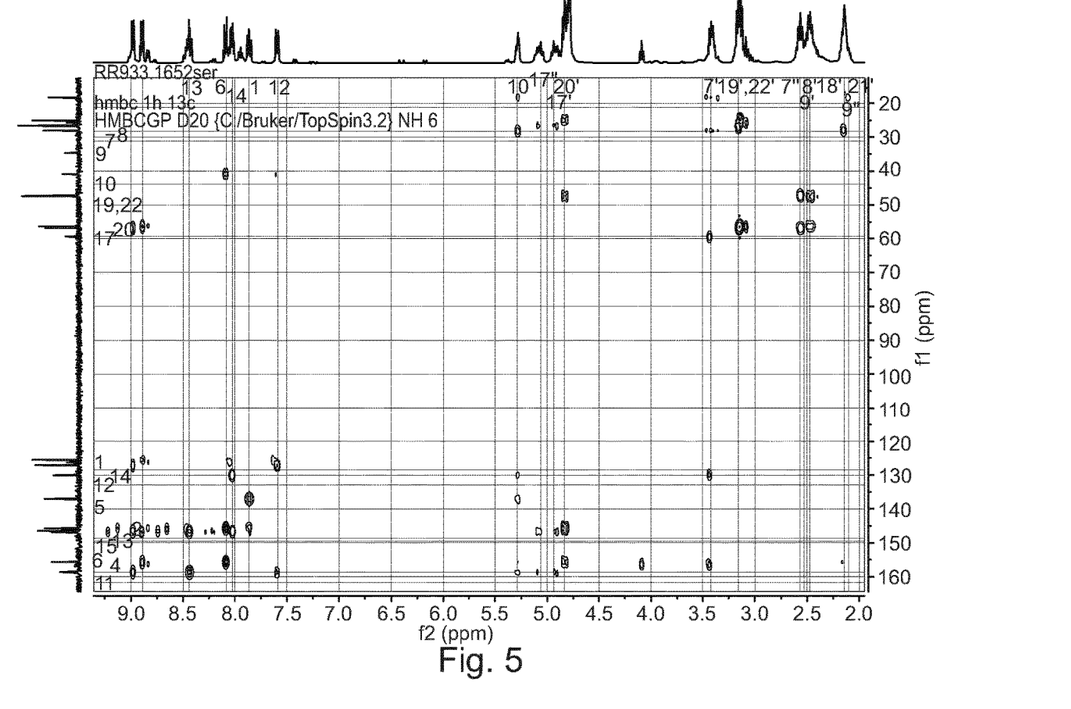
FIG. 5: 2D-NMR-spectrum of reaction mixture.

2D-NMR
Results are shown in FIG. 5 at the end of the reaction. The results show that a compound of formula (IV) (called "dimer 1") is formed.

Figure 6:
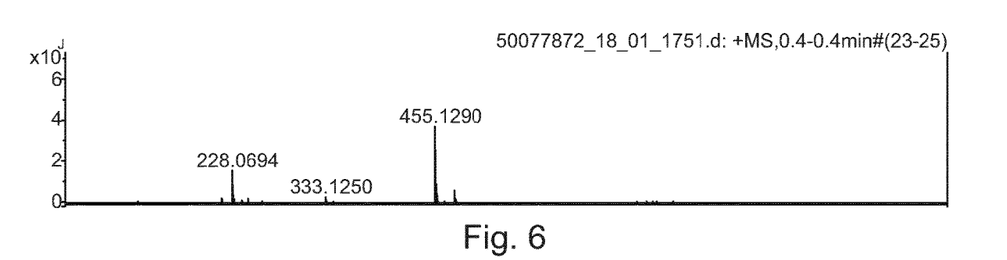
FIG. 6: LC/HPLC-NMR-spectrum of reaction mixture.

LC/HPLC:
Results are shown in FIG. 6 at the end of the reaction. The results show that separation of monomer and dimer is possible. LC-UV confirms the UV spectra of individual peaks for the two substances (cf. supra). LC-MS confirms the M/z=455 peak corresponding to the dimer. The method allows qualitative observation only, quantification is not possible since some dimer could be formed in the gas phase as ionic complex, as observed for PPS reference (PPS=SPV-vinyl), which cannot form a chemical dimer by cycloaddition.

Example 2

(Comparative): Ni Bath with Compound of Formula (Ill)

Figure 7:
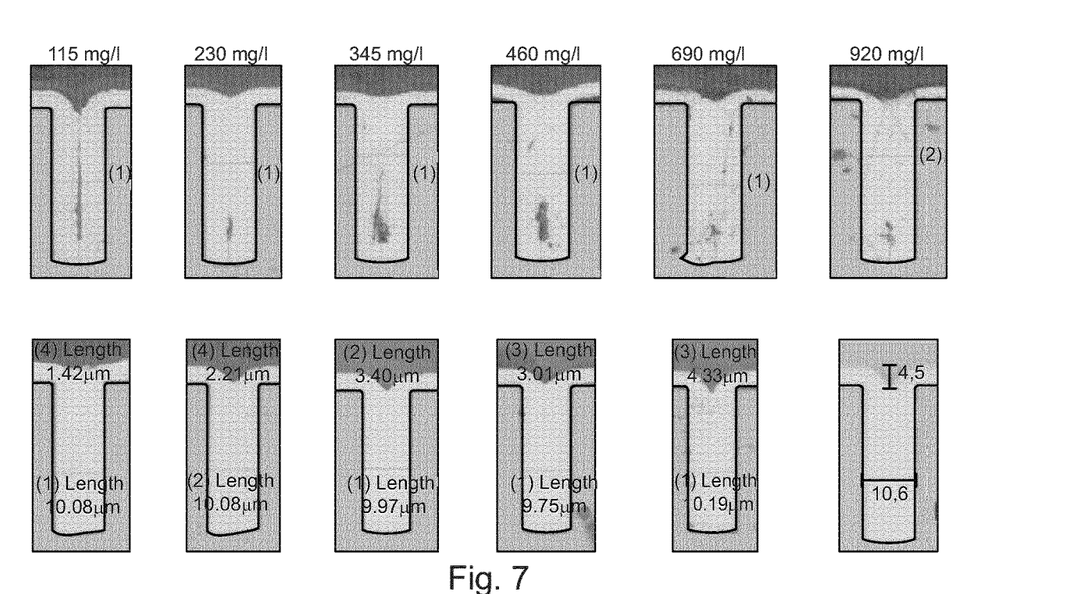
FIG. 7: shows the filling of micro via (vertical interconnect access) with a Ni-bath with compound of formula (III) and with a dimer of formula (IV).

TSV substrate with 10×30 μm vias,
2 ASD (ampere per square decimeter),
10 min
50° C.
100 rpm stirring
Standard Spherolyte Ni VMS bath (70 g/L Ni, 5 g/L Chloride) with boric acid reduced to 30 g/l, comprising a compound of formula (III). Amounts of the compound of formula (III) were between 115 mg/L-920 mg/L.
The results are shown in FIG. 7, first line of pictures.

Example 3

(Inventive): Ni Bath with Dimer of Compound of Formula (IV)

The same bath and conditions were employed as in Example 2, but a compound of formula (IV) was used as predominant additive, obtained according to example 1. Some compound of formula (III) was still present (about 10 weight-%, based on the total amount of (IV)).

The results are shown in FIG. 7, second (lower) line of pictures. Less voids can be seen in the filling structure in comparison to example 2. Moreover, faster deposition and filling was observed in comparison to example 2.

The invention claimed is:

1. An aqueous bath comprising
a source of nickel ions, and optionally a source of ions of at least one alloying metal,
at least one buffering agent,
at least one of a dimer of a compound of formula (I) or mixtures thereof formula (I)

wherein
$R_1$ is a substituted or unsubstituted alkenyl group,
$R_2$ may be present or not, so that the nitrogen may be positively charged or not, and $R_2$, if present, is a —$(CH_2)_n$—$SO_3^-$ group, wherein n is an integer in the range of 1-6, wherein one or more of the hydrogens in the —$(CH_2)_n$—$SO_3^-$ group may be replaced by a substituent,
wherein the at least one of a dimer of a compound of formula (I) or mixtures thereof comprises a compound of formula (II)

formula (II)

2. The aqueous bath of claim 1, wherein the total concentration of the at least one of a dimer is 1-10000 mg/L.

3. The aqueous bath of claim 1, wherein the alloying metal is selected from cobalt or iron or a combination thereof.

4. An aqueous bath comprising
a source of nickel ions, and optionally a source of ions of at least one alloying metal,
at least one buffering agent,
at least one of a dimer of a compound of formula (I) or mixtures thereof formula (I)

wherein
$R_1$ is a substituted or unsubstituted alkenyl group,
$R_2$ may be present or not, so that the nitrogen may be positively charged or not, and $R_2$, if present, is a —$(CH_2)_n$—$SO_3^-$ group, wherein n is an integer in the range of 1-6, wherein one or more of the hydrogens in the —$(CH_2)_n$—$SO_3^-$ group may be replaced by a substituent, wherein the compound of formula (I) comprises a compound of formula (III)

formula (III)

5. The aqueous bath of claim 4, wherein the dimer of the compound of formula (III) is a compound of formula (IV)

formula (IV)

6. The aqueous bath of claim 4, wherein the total concentration of the at least one of a dimer is 1-10000 mg/L.

7. The aqueous bath of claim 4, wherein the alloying metal is selected from cobalt or iron or a combination thereof.

8. A compound of formula (II)

formula (II)

wherein $R_2$ is a —$(CH_2)_n$—$SO_3^-$ group, wherein n is an integer in the range of 1-6, and wherein one or more of the hydrogens in the —$(CH_2)_n$—$SO_3^-$ group may be replaced by a substituent.

9. The compound of claim 8, which is a compound of formula (IV)

formula (IV)

* * * * *